US009633174B2

(12) United States Patent
Nichols

(10) Patent No.: US 9,633,174 B2
(45) Date of Patent: Apr. 25, 2017

(54) SYSTEM, METHOD AND COMPUTER PROGRAM PRODUCT FOR PROVIDING A HEALTHCARE USER INTERFACE AND INCENTIVES

(71) Applicant: Optum, Inc., Minnetonka, MN (US)

(72) Inventor: Matt Nichols, Buffalo, MN (US)

(73) Assignee: OPTUM, INC., Minnetonka, MN (US)

( * ) Notice: Subject to any disclaimer, the term of this patent is extended or adjusted under 35 U.S.C. 154(b) by 135 days.

(21) Appl. No.: 14/180,694

(22) Filed: Feb. 14, 2014

(65) Prior Publication Data
US 2015/0235006 A1    Aug. 20, 2015

(51) Int. Cl.
*G06Q 10/10*    (2012.01)
*G06Q 30/02*    (2012.01)
(Continued)

(52) U.S. Cl.
CPC ........ *G06F 19/3475* (2013.01); *A61B 5/0002* (2013.01); *A61B 5/7275* (2013.01);
(Continued)

(58) Field of Classification Search
CPC ... A61B 5/0002; A61B 5/4833; A61B 5/7275; G06Q 30/02; G06Q 30/0224;
(Continued)

(56) References Cited

U.S. PATENT DOCUMENTS

| 6,039,688 | A  | * | 3/2000 | Douglas | .............. | G06F 19/3475 |
|---|---|---|---|---|---|---|
|  |  |  |  |  |  | 128/921 |
| 7,925,519 | B2 | * | 4/2011 | Greene | ................. | G06F 19/328 |
|  |  |  |  |  |  | 705/2 |

(Continued)

OTHER PUBLICATIONS

Peppet, Scott R., Unraveling Privacy: The Personal Prospectus & the Threat of a Full Disclosure Future (Aug. 7, 2010). Northwestern University Law Review, 2011 . Available at SSRN: http://ssrn.com/abstract=1678634.*

(Continued)

*Primary Examiner* — Nikolai A Gishnock
(74) *Attorney, Agent, or Firm* — Dorsey & Whitney LLP

(57) ABSTRACT

Actively engaging members in managing their own healthcare, improving their health, and reducing healthcare costs to the payer involves providing a unified interface for member engagement. The interface may be communicatively coupled with a healthcare system, may be personalized to the member, and may offer multiple possible rewards to the member to encourage member behavior to effectively reduce healthcare costs and improve the quality of healthcare plans. The interface may provide the member with a pathway guiding the member to engage in activities to achieve short-term, intermediate and long-term goals for which actions are presented. Goals or actions may be predefined and may additionally be selected by the member. When member-engagement in the actions is verified, rewards may be granted to the member's account. In connection with such member engagement, the healthcare system collects member information, applies rules to that information, and generates alerts from those rules.

20 Claims, 8 Drawing Sheets

(51) Int. Cl.
*G06F 19/00* (2011.01)
*A61B 5/00* (2006.01)

(52) U.S. Cl.
CPC .......... *G06F 19/324* (2013.01); *G06F 19/328* (2013.01); *G06F 19/345* (2013.01); *G06F 19/3418* (2013.01); *G06F 19/3431* (2013.01); *G06F 19/3456* (2013.01); *G06F 19/3481* (2013.01); *G06F 19/3487* (2013.01); *G06F 19/363* (2013.01)

(58) Field of Classification Search
CPC .... G06Q 30/0226; G06Q 40/08; G06Q 50/22; G06Q 50/24; G06F 19/324; G06F 19/3418; G06F 19/3431; G06F 19/3481; G06F 19/345; G06F 19/363
USPC ............. 705/1, 2, 14.2, 14.17, 14.19, 14.25; 434/262
See application file for complete search history.

(56) References Cited

U.S. PATENT DOCUMENTS

| | | | | |
|---|---|---|---|---|
| 8,714,983 | B2* | 5/2014 | Kil | G06F 19/345 434/236 |
| 9,035,765 | B2* | 5/2015 | Engelhard | G06Q 50/24 222/183 |
| 2005/0102172 | A1* | 5/2005 | Sirmans | G06Q 40/08 705/4 |
| 2006/0095299 | A1* | 5/2006 | Hilliard | G06Q 10/06398 705/2 |
| 2006/0111944 | A1* | 5/2006 | Sirmans | G06Q 30/0209 705/3 |
| 2006/0129458 | A1* | 6/2006 | Maggio | G06Q 30/02 705/14.2 |
| 2006/0253330 | A1* | 11/2006 | Maggio | G06Q 30/02 705/14.2 |
| 2006/0282319 | A1* | 12/2006 | Maggio | G06Q 30/02 705/14.19 |
| 2008/0103910 | A1* | 5/2008 | Gardenswartz | G06Q 10/04 705/14.25 |
| 2008/0147481 | A1* | 6/2008 | Robinson | G06Q 20/40 |
| 2008/0147502 | A1* | 6/2008 | Baker | G06Q 30/0225 705/14.26 |
| 2008/0183502 | A1* | 7/2008 | Dicks | G06F 19/3418 705/3 |
| 2008/0262866 | A1* | 10/2008 | Greene | G06Q 10/087 705/2 |
| 2010/0249531 | A1* | 9/2010 | Hanlon | G06Q 10/04 600/300 |
| 2011/0125517 | A1* | 5/2011 | Dhoble | G06F 19/322 705/2 |
| 2011/0145747 | A1* | 6/2011 | Wong | A61B 5/0002 715/771 |
| 2011/0246272 | A1* | 10/2011 | Joa | G06Q 30/0215 705/14.17 |
| 2011/0246279 | A1* | 10/2011 | Joa | G06Q 30/02 705/14.25 |
| 2011/0251853 | A1* | 10/2011 | Greene | G06Q 10/087 705/2 |
| 2012/0173398 | A1 | 7/2012 | Sjodin et al. | |
| 2012/0310661 | A1* | 12/2012 | Greene | G06Q 10/087 705/2 |
| 2013/0046227 | A1* | 2/2013 | Hyde | G06Q 50/22 604/20 |
| 2013/0046555 | A1* | 2/2013 | Hyde | G06Q 50/22 705/3 |
| 2013/0080184 | A1* | 3/2013 | Streat | G06Q 50/24 705/2 |
| 2013/0204410 | A1* | 8/2013 | Napolitano | G06F 19/3481 700/91 |
| 2014/0372133 | A1* | 12/2014 | Austrum | G06F 19/3431 705/2 |
| 2016/0063532 | A1* | 3/2016 | Loeb | G06Q 30/0234 705/14.25 |
| 2016/0132660 | A1* | 5/2016 | Barajas | G06Q 10/10 705/2 |

OTHER PUBLICATIONS

"Medical Marketing Guidelines: For Medicare Advantage Plans, Medicare Advantage Prescription Drug Plans, Prescription Drug Plans, and 1876 Cost Plans", Chapter 3, Rev. 106, Jun. 22, 2012. (116 pages).

* cited by examiner

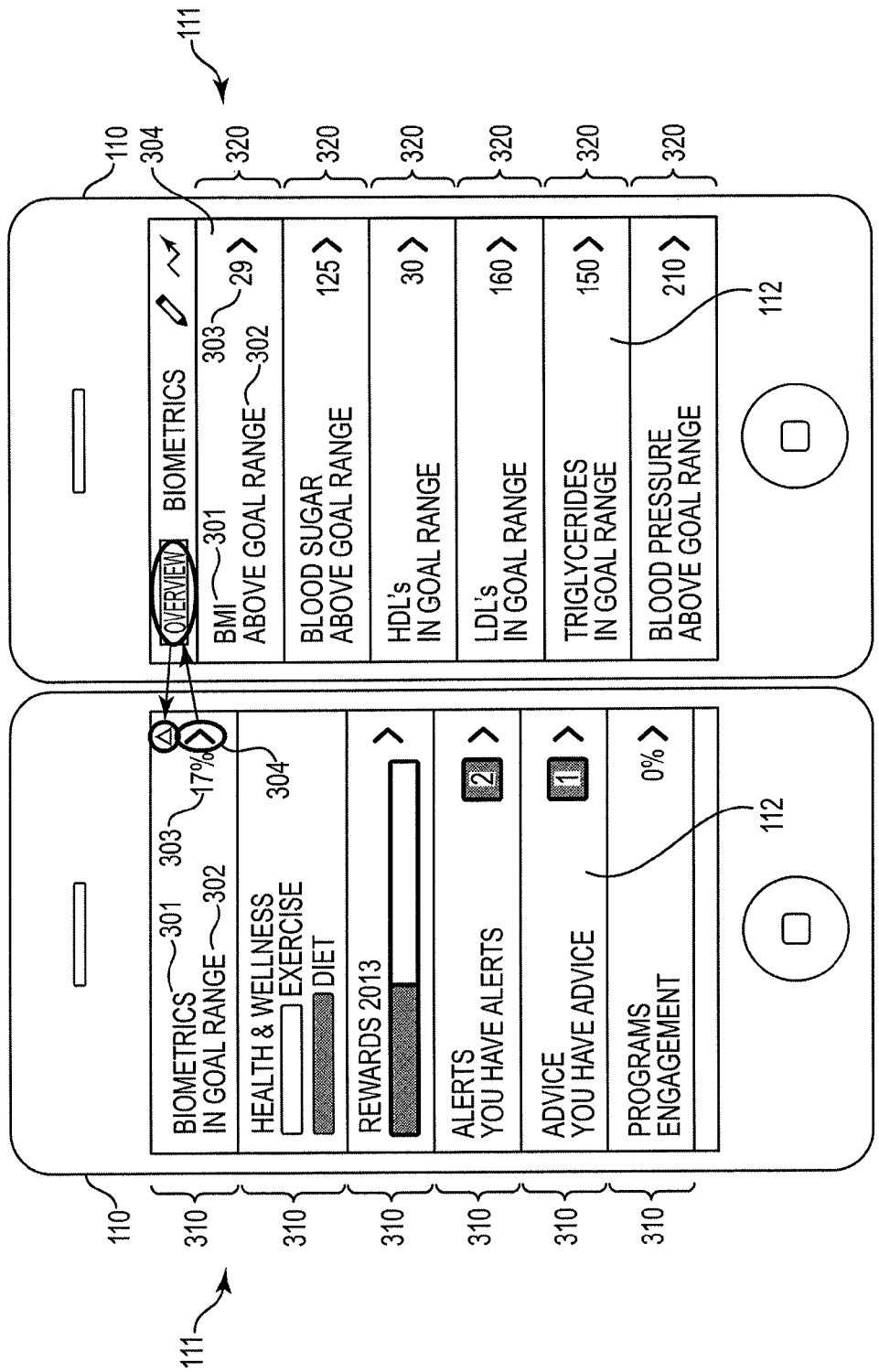

SYSTEM, METHOD AND COMPUTER PROGRAM PRODUCT FOR PROVIDING A HEALTHCARE USER INTERFACE AND INCENTIVES

BACKGROUND

Field of the Disclosure

This application generally relates to healthcare and providing a user interface for engagement in a healthcare program and related incentives.

Background of the Disclosure

Rising healthcare costs lead to a desire by payers (such as employers and insurers) that their members (such as employees and their families) become more engaged and participate more actively in managing their health. For example, if a pool of members includes a substantial fraction who are obese, there would be substantial costs associated with heart problems that could likely result. If these members, or even some of them, could be convinced to make healthy lifestyle changes, such as losing weight and increasing exercise, they would become healthier. This would have the effect that members develop fewer and less severe heart problems. Providers would be happier with a healthier member population. Payers would benefit with consequential reduction in cost.

A first known solution is for health insurers to educate members, encourage them to adopt healthy lifestyles, and remind them about activities that would assist in member healthcare. These can include a plethora of possibilities, such as posters, mailings, nurse response lines, reminder calls about appointments, and otherwise. While these activities can promote the general goal of raising member awareness of healthcare needs, they can be subject to some drawbacks. Members receiving the information may find it too complex, overly-diverse, contradictory or redundant. It sometimes occurs that members remain unaware of important healthcare issues or unresponsive due to members ignoring excessive efforts at member outreach by payers or due to the outreach being delivered through channels of which the member is unaware. It sometimes occurs that these techniques are not personalized to the member's particular healthcare needs. These techniques might also tend to frustrate members, have high costs, and produce relatively minimal outcomes.

A second known solution is for members to seek out healthcare information, such as by using the Internet or one (or more) of the many healthcare applications (sometimes called "apps") available for smartphones, tablets, or other computing devices. Members can sometimes obtain a relatively large amount of information from search engines, health and wellness portals, health and wellness applications, and from email and other communication with payers. While these activities also can also promote the general goal of raising member awareness of healthcare needs, they are also subject to some drawbacks. Similar to the first known solution, it sometimes occurs that members receive information that is too complex, overly-diverse, contradictory or redundant, and it sometimes occurs that members remain unaware of or unresponsive to important healthcare issues. Moreover, these techniques sometimes lead to members obtaining or believing healthcare information that is erroneous, not up to date, or misleading.

A third known solution is for members to obtain healthcare information directly from providers during visits. For example, a member might get advice from their doctor about keeping their cholesterol level down, while at a regular checkup. While this can also promote the general goal of raising member awareness of healthcare solutions, it is also subject to some drawbacks. It sometimes occurs that the doctor has many other patients scheduled for that day, and so cannot take the time for a proper review. The doctor may be focused on the specific issues the member arrived for, and so cannot take the time to review the member's longitudinal history. In some cases the member's questions would be better addressed by a different medical professional, such as a nutritionist. In this latter case, the member is burdened with having to schedule yet another appointment, at a different time and possibly a different facility, with the effect of frustrating the member and reducing the likelihood of the member becoming engaged in their own healthcare.

Each of these examples, as well as other possible considerations, can cause difficulty in healthcare aspects including costs, quality, outcomes, and engaging members in actively managing their own healthcare.

BRIEF SUMMARY OF THE DISCLOSURE

This application provides apparatuses and techniques that can enable members to actively engage in managing their own healthcare, and to, by the member's behavior, improve their health and reduce healthcare costs to the payer and the member. This application also provides apparatuses and techniques that can enable the member to receive a simplified and unified interface to their healthcare system, which can be personalized to the history and status of the member, and that can provide a variety of possible action alerts and related rewards to the member, to encourage member behavior that is effective in reducing healthcare costs.

In one embodiment, the apparatuses and techniques can provide guidance and describe progress to the member with an application (or "app") with a convenient user interface (UI) in the form of a pathway, in which the member can be able to set intermediate goals, actions and alerts can be presented to the member, and when those actions by the member are verified, can provide the member with a selection of rewards. These intermediate goals, actions and alerts can provide the member with a unified interface, collecting for the member personalized, timely information with respect to what to do, and when to do it, to maintain their best health and quality of life.

In one embodiment, the apparatuses and techniques can be responsive to information about the member, can apply a set of rules to that information, and can generate alerts in response to application of those rules. The information about the member can be collected from disparate sources, including reports of insurance and flexible spending account (FSA) claims, reports from medical personnel (such as with respect to visits and procedures, chart notes, observations and diagnoses, and otherwise), reports from laboratory technicians (such as with respect to laboratory visits and procedures, chart notes, laboratory observations and diagnoses, and otherwise), reports from physical therapists and other professionals (such as with respect to visits and procedures, and measurements), reports from pharmacists (such as with respect to filled prescriptions), reports from biometric devices (such as measurements of blood pressure, cholesterol, glucose level, weight, and otherwise), self-reports from members (such as with respect to diet and exercise), and reports derived from the user interface (such as which intermediate goals are set by the user). The rules applied to that information can include medical rules (such as derived from evidence-based medicine), business rules (such as programs or promotions offered by payers to encourage selected behaviors), and otherwise. The alerts generated in response to those rules can include messages displayed by the UI (such as when the member logs in to the application).

In one embodiment, the apparatuses and techniques can provide one or more alerts that prompt healthy actions by the member, which upon verification, mean the apparatuses and techniques can make available one or more rewards to the member. Rewards can include positive recognition of the member, "points" that can be exchanged by the member for other items of value, money, rebates of co-pays or other fees, lowered insurance rates, free or discounted consumer goods, and other things of value.

After reading this application, those skilled in the art would recognize that techniques shown in this application are applicable to more than just the specific embodiments shown herein. For a first example, the concept of healthcare activities is intended to be broad, and can include medical and dental activity, nutrition and exercise, mental health, physical therapy and other therapies, and promoting check-ups (such as prenatal and well baby care). For a second example, healthcare activities could be replaced or augmented with any other activity the payer desires to encourage or discourage, including workplace activities such as accident/safety awareness, short and long-term disability prevention and management, or otherwise.

While multiple embodiments are disclosed, including variations thereof, still other embodiments of the present application will become apparent to those skilled in the art from the following detailed description, which shows and describes illustrative embodiments of the application. The application is capable of modifications in various aspects, all without departing from its scope or spirit. The drawings and detailed description are illustrative in nature and not restrictive.

BRIEF DESCRIPTION OF THE FIGURES

FIGS. 3A and 3B illustrate a user interface for use by a member according to exemplary embodiments of the present disclosure.

DETAILED DESCRIPTION

Terms and Phrases

Figure 1:
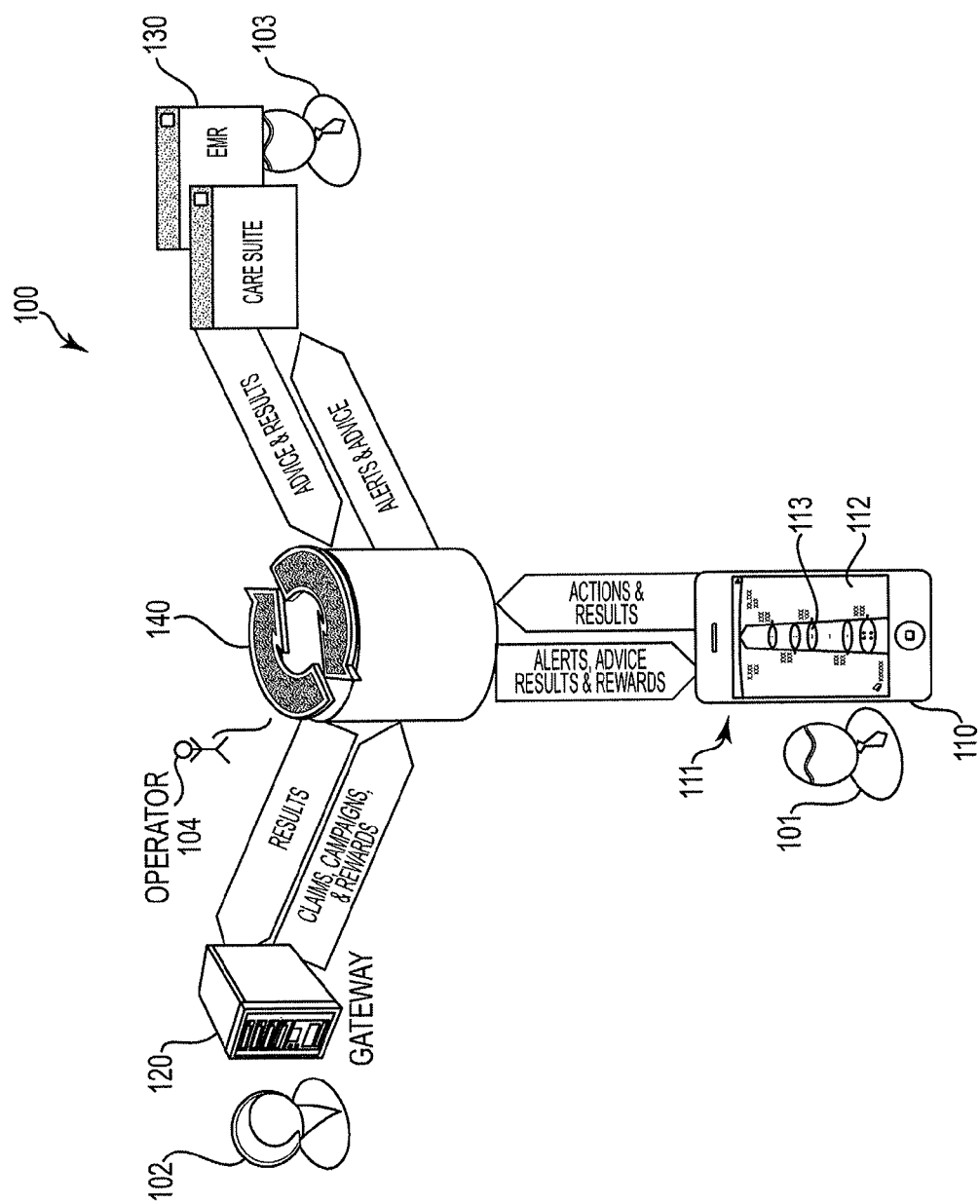
FIG. 1 is a diagram of a system for administering a rewards program according to exemplary embodiments of the present disclosure.

The following definitions are intended to be exemplary and illustrative, not necessarily limiting:

The terms "member", "employee", "insured", "patient", "user", and variants thereof, generally refer to any person or family unit with respect to whom the payer desires decreased healthcare costs, the provider desires improved health and healthcare, and the member desires improved health and lifestyle along with decreased costs or increased rewards. When medical providers are providing healthcare services to the member, the term member can include any person in the covered family unit or other group. When rewards are provided to the member, the rewards can be provided to individual persons in the covered family unit or other group, or if so determined by the payer, can be aggregated by the covered family unit or other group.

The terms "payer", "employer", "insurer", and variants thereof, generally refer to any entity, such as an employer of the member, or an insurance or reinsurance company, or government entity responsible for paying a substantial fraction of healthcare costs (excluding "co-pay" amounts generally assessed against the member), or otherwise subject to economic harm from member health problems (such as an organization that would suffer from the member's absence).

The terms "insurance", "insurance benefits", "health insurance", and variants thereof, generally refer to any benefit, such as payment for provider services (excluding "co-pay" amounts generally assessed against the member), including without limitation a negotiated lower rate for provider services, payment for most of the cost of provider services, provider services offered at no cost to the member to encourage healthy behavior, and otherwise.

The terms "provider", "medical personnel", "doctor", "hospital", "laboratory technician", "nurse", "physical therapist", and variants thereof, generally refer to any provider of one or more healthcare services.

The terms "healthcare", "healthcare services", "medical procedure", "office visit", "therapy", and variants thereof, generally refer to provision of healthcare services. The concept and scope of healthcare activities is intended to be broad, and can include medical and dental activity, nutrition advice and exercise coaching, mental health services and counseling, physical therapy, chiropractic, acupuncture, aromatherapy, other non-Western therapies, and other therapies, and includes promoting periodic and aperiodic checkups (such as prenatal and well baby care), healthy diet, regular exercise, and age-appropriate and gender-appropriate testing.

The terms "points", "miles", "credits", and variants thereof, generally refer to any credit to, or debit from, a member, that can be converted into any thing of value. For example, points that can be exchanged, once a designated amount of them are reached, for rewards of any kind (as described herein), would be included.

The terms "reward", "award", "rebate", and variants thereof; generally refer to any thing of value, including money, securities, rebates or refunds of funds already paid in (such as regular health insurance payments), reduced costs for any thing of value (such as reduced health insurance rates for the future), consumer goods, consumer supplies, airline or other travel tickets, sports or other events tickets, coupons for discounted goods or services, things of value conditioned substantially on chance (such as lottery tickets or a chance to win a new car), "perks" (such as a good parking spot), recognition (such as an award or announcement of achievement), or anything else a member might think has value.

The terms "reward program", "reward campaign", "campaign", and variants thereof, generally refer to any plan, designed or adopted by the payer, for providing rewards to members, when those members follow the actions indicated by the healthcare incentives and earn "points" and "miles" that they can exchange for things of value. In some cases the reward program might be limited by relevant law or regulation, such as the CMS reward guidelines promulgated at 42

CFR 422.2268 and 42 CFR 423.2268, and summarized in CMS Medicare Guidelines on Rewards, §70.2.

Figures and Text

Healthcare Incentive System

FIG. 1 is a diagram of a system for administering a rewards program according to exemplary embodiments of the present disclosure.

The system 100 includes elements shown in the figure, including at least a member workstation 110 disposed to be used by a member 101, a payer workstation 120 disposed to be used by a payer 102, a provider workstation 130 disposed to be used by a provider 103, and a database/analytics system 140 disposed to be used by an operator 104. The system 100 can also include one or more communication links disposed to carry messages between and among the member workstation 110, the payer workstation 120, the provider workstation 130, and any other devices coupled to the system 100. For example, the communication links can include Internet connections, and the member workstation 110, the payer workstation 120, the provider workstation 130, and any other devices coupled to the system 100, can communicate using the Internet, such as using the HTTP or HTTPS protocols, or variants thereof, themselves using the TCP/IP protocols, or variants thereof, themselves using (at least in the case of the member workstation 110) the IEEE 802.11 family, or variants thereof.

The elements of the system 100 can include any devices appropriate to the functions described herein, disposed (such as by programming) to perform those functions. For a first example, the member workstation 110 can include a "smartphone", such as a cellular telephone or tablet (such as an iPhone™, iPad™, or a device using an Android OS) capable of sending and receiving voice and data, and including a screen 111 capable of presenting a user interface 112, and optionally including touch-sensitive buttons 113 (as the user interface 112 is further described herein). For a second example, the payer workstation 120 and the database/analytics system 140 can each include a server, such as a web server coupled to the Internet and disposed to interact with (at least) the user workstation 110 and (optionally) the provider workstation 130 and each other. The payer workstation 120, the provider workstation 130, and the database/analytics system 140 can communicate using the Internet at web communication ports or other communication ports, or may alternatively eschew the Internet and use other communication techniques.

As further described herein, data flow within the system 100 includes communication between and among all four of the member workstation 110, the payer workstation 120, the provider workstation 130, and the database/analytics system 140.

The member 101, using the member workstation 110, engages with the system 100 with respect to health-related actions, such as by receiving advice and alerts from the payer workstation 120 or the provider workstation 130, electing particular health programs, electing and conducting some of the actions recommended by those programs (e.g., via electronic links, contact information, a scheduling feature or live chat) such as scheduling a biometrics screening test, and reports on other actions recommended by those programs (such as reporting having exercised, or reporting having taken a dose of prescribed medication). In some cases, the member 101 can engage with the system 100 by coupling a biometric device (not shown in this figure) to the member workstation 110, and allowing the device to generate clinical data and report biometric measurements to the system 100. The member 101 may also earn "points" or "miles", as further described herein, by participating in surveys suggested by the payer 102 or the provider 103. The member 101, having earned and accumulated "points" or "miles", may elect one or more rewards by virtue of having earned those "points" or "miles".

Medical data from the member 101 can be sent to the provider workstation 130, which can aid the provider 103 in making sound medical decisions and in advising the member 101. For example, the provider 103 might observe from the member's medical data that the member 101 should have a dosage change for a particular medication; the provider 103 can send an alert informing the member 101 and requesting that the member 101 refill the prescription, and can also send an alert to the member's pharmacy (a different provider 103) informing them of the prescription change. In some embodiments, medical data may also be sent to the payer workstation 120, which aids the payer 102 in making sound financial decisions in setting insurance rates for the member 101. For example, successful completion of a smoking-cessation program, or a weight-loss program, might allow the payer 102 to determine that the member 101 represents a lesser risk of medical costs, and can lower rates for the member 101. Alternatively, successful program completion might allow the member 101 to select lower co-pays as the member's reward. In some embodiments, the database/analytics system 140 might also receive medical data from the member 101, for the purpose of aggregating that information, and possibly determining which rewards are most effective at reducing healthcare cost, after adjusting for other statistical factors.

Alternatively, medical data or self-reported data from the member 101 can be withheld from the payer 102, and only reported to the payer 102 in a statistically aggregate, or otherwise anonymous way (such as by the provider 103 or by the database/analytics system 140), so that the payer 102 can make sound financial decisions, but cannot obtain information on the medical condition of any particular member 101.

The payer 102, using the payer workstation 120, engages with the system 100 with respect to financial actions, such as by receiving aggregated medical data, as described above, and such as by responding to individual claims, and by generating and publicizing new rewards or new campaigns for health improvement. For example, if the payer 102 identifies back injuries as a particular safety hazard at the workplace, with the statistical effect that reduction in back injuries would reduce healthcare cost, the payer 102 can create a new program for proper lifting techniques, or alternatively, for team lifting or forklift use, and can publicize this new program to members 101 using alerts. Similarly, if the payer 102 identifies a particular disease as being reported with unexpectedly high frequency, the payer 102 can send information to providers 103 to look out for early signs of that disease, and can publicize that information to providers 103 using alerts. The payer 102 might even reward providers 103 who are able to make early identifications and head off the more expensive stages of the disease, by rewarding providers 103 with a providers' reward program, similar to rewarding members 101 with the members' reward programs primarily described herein. The payer 102 also engages with the system 100 whenever a member 101 is able to claim a reward (or when a provider 103 is able to claim a provider's reward), such as by issuing payment for that reward, or in those cases of payers 102 who are employers and rewards that are employer "perks", directly providing the reward.

In some cases the reward program or campaign might be limited by relevant law or regulation, such as the CMS reward guidelines promulgated at 42 CFR 422.2268 and 42 CFR 423.2268, and summarized in CMS Medicare Guidelines on Rewards, §70.2. In some cases the reward program or campaign might be designed to be similar to health insurance and insurance benefits coverage available to the member, so as to reduce claims against those insurance benefits. In some cases the reward program or campaign might be encouraged by the employer's insurance company, as a condition of allowing the employer price breaks or rebates on insurance paid by the employer. Aspects of an exemplary reporting portal are described in a co-pending application having at least one common inventor having the Ser. No. 13/875,516, entitled "CMS Stars Rating Data Management," and filed on May 2, 2013, the content of which is incorporated by reference in its entirety for any useful purpose.

The provider 103, using the provider workstation 130, engages with the system 100 with respect to medical actions, such as by receiving medical data for individual members 101, as described above, as well as aggregated medical data for member populations and sub-populations, as described above. Both the payer 102 and the provider 103 can generate surveys and publicize them to members 101 using alerts, and can collect the data either directly from members 101, or indirectly from the database/analytics system 140. The provider 103 can also provide encouragement as a quasi-reward to members 101, such as by noticing whenever a particular member 101 hits the next goal in their elected long-term program, and congratulating those members 101 with personalized messages.

In these interactions in which the member 101, the payer 102, or the provider 103 engage with the system 100, the system 100 is, providing information that is personalized to the particular member 101 as a patient, and also accounts for longitudinal effects of the member's behavior as a future patient. This has the effect that the system 100 provides a member-centric set of information, and in particular, a member-centric user interface 112 at the place of engagement between the member 101 and the system 100. This also has the effect that the system 100 provides a longitudinal set of information (and in particular, a detailed medical and behavioral history) with respect to the member's behavior and the medical condition thereof. This also has the effect that the system 100 encourages members' behavior, both individually and in the aggregate, that tends to improve members' health, and that tends to reduce healthcare costs to the payer 102, and in particular, that the payer 102 regards as cost-effective in reducing healthcare costs. For example, by encouraging healthy behavior by members, it might be possible for the payer to expand the benefits available according to the member's healthcare insurance, such as by one or more of reducing co-pay amounts, covering additional medical providers, covering additional procedures by medical providers, covering additional medications or reducing co-pay amounts for those medications. In addition, by reducing healthcare costs to the payer through member engagement in their health, the rating and quality of a healthcare plan may be improved.

Figure 2A:
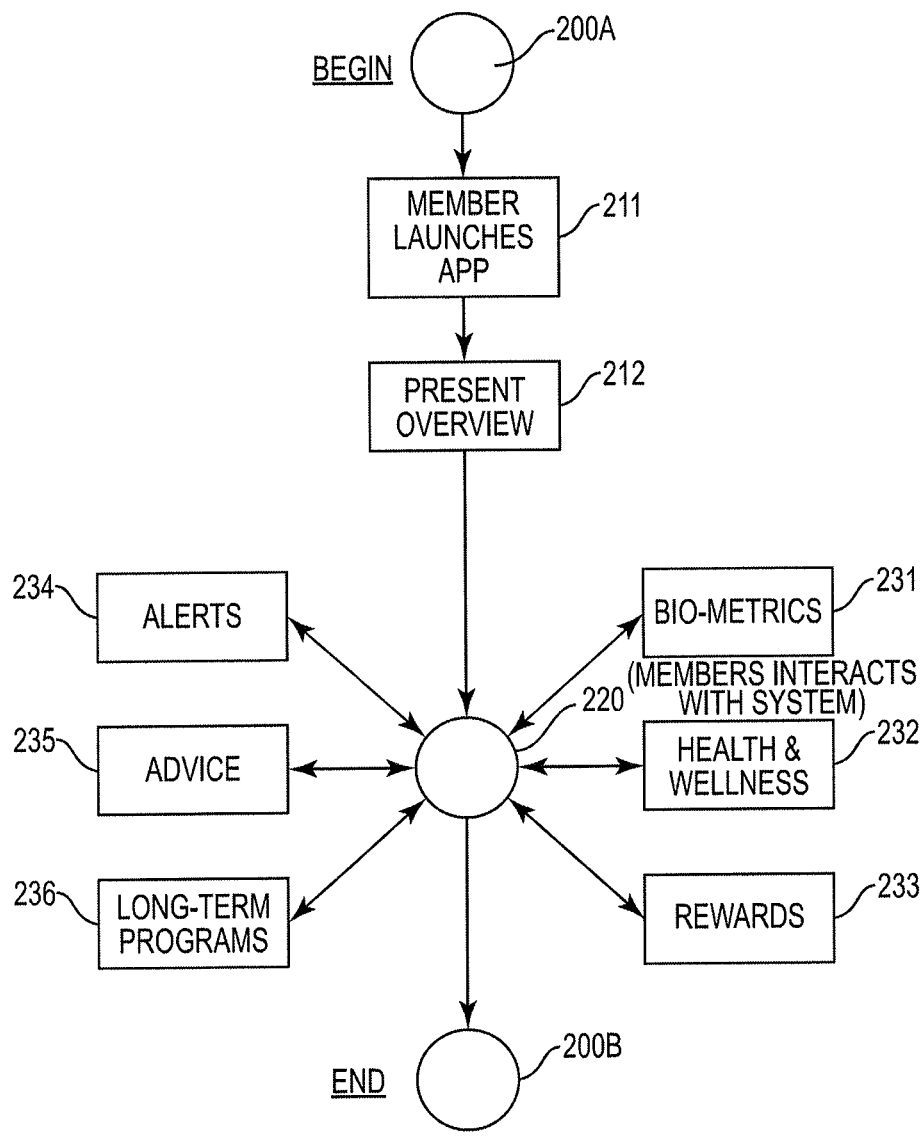
FIG. 2A shows a flow diagram of a method of member engagement with the system of FIG. 1 according to exemplary embodiments of the present disclosure.

The database/analytics system 140 may be operated by an operator 104 of the system. In some cases the operator 104 may be a provider party, a payer party or a third party, and the database/analytics system 140 may be updated and maintained by any of these parties. The database/analytics system 140 may receive member information Method of Providing Healthcare Incentives FIG. 2A illustrates a flowchart of a method 200 of providing healthcare incentives according to the present disclosure.

The method 200 can be performed by the system 100 and its elements, such as one or more members 101 at member workstations 110, one or more payers 102 at payer workstations 120, one or more providers 103 at provider workstations 130, and the database/analytics system 140, or combinations thereof. Where described herein that a step is performed by the method 200, it should be understood from context (or from the figure) which element of the system 100, takes the specific actions described for that step.

Although the steps are shown in a particular order, in the context of the invention, there is no reason for any such limitation. The steps may be performed in a different order, or may be performed in a parallel or pipelined manner, or otherwise.

A flow point 200A indicates a beginning of the method 200.

At a step 211, the member 101 launches the user interface app at their member workstation 110, and logs in to their individual account at the database/analytics system 140, with a username, and a password. In alternative embodiments, other forms of security may be used to protect the member's medical information from improper exposure, such as facial recognition (using an attached camera at the member workstation 110), fingerprint detection, retinal identification, typing speed detection, or some other security system. Two-factor authentication may optionally be required.

Since this step 211 involves using a particular app at the member workstation 110, the app will have been loaded onto the member workstation 110 at some earlier time. For example, the member 101 might have downloaded and installed the app on the member workstation 110, or the member workstation 110 might have been purchased with the app pre-installed. In alternative embodiments, there might be no such requirement for an app, and the database/analytics system 140 (or the payer workstation 120, or the provider workstation 130) might perform as a web server and emulate the user interface 112 described herein. In the context of the invention, there is no particular requirement for using an app, or a smartphone, or even the user interface 112 described herein. For example, the member 101 might optionally re-skin the app, with the effect of providing a completely different look and feel.

At a step 212, the user interface 112 presents the member 101 with an overview, as further described with respect to FIGS. 3A and 3B. The overview can include a summary of the member's biometrics information, a summary of the member's health and wellness information, a summary of the member's rewards points, a summary of the member's alerts/advice awaiting receipt by the member 101, and a summary of the member's engagement with long-term programs, all as further described with respect to FIGS. 3A and 3B.

At a flow point 220, the member 101 is ready to interact with the system 100, using the user interface 112, with the effect of engaging with the system 100. The member 101 can conduct a substantial number of individual interactions with the system 100, with the effect that the member 101 exchanges information with the system 100. From the overview, the system 100 is ready to present other parts of the user interface 112, as further described herein.

Figure 4A:
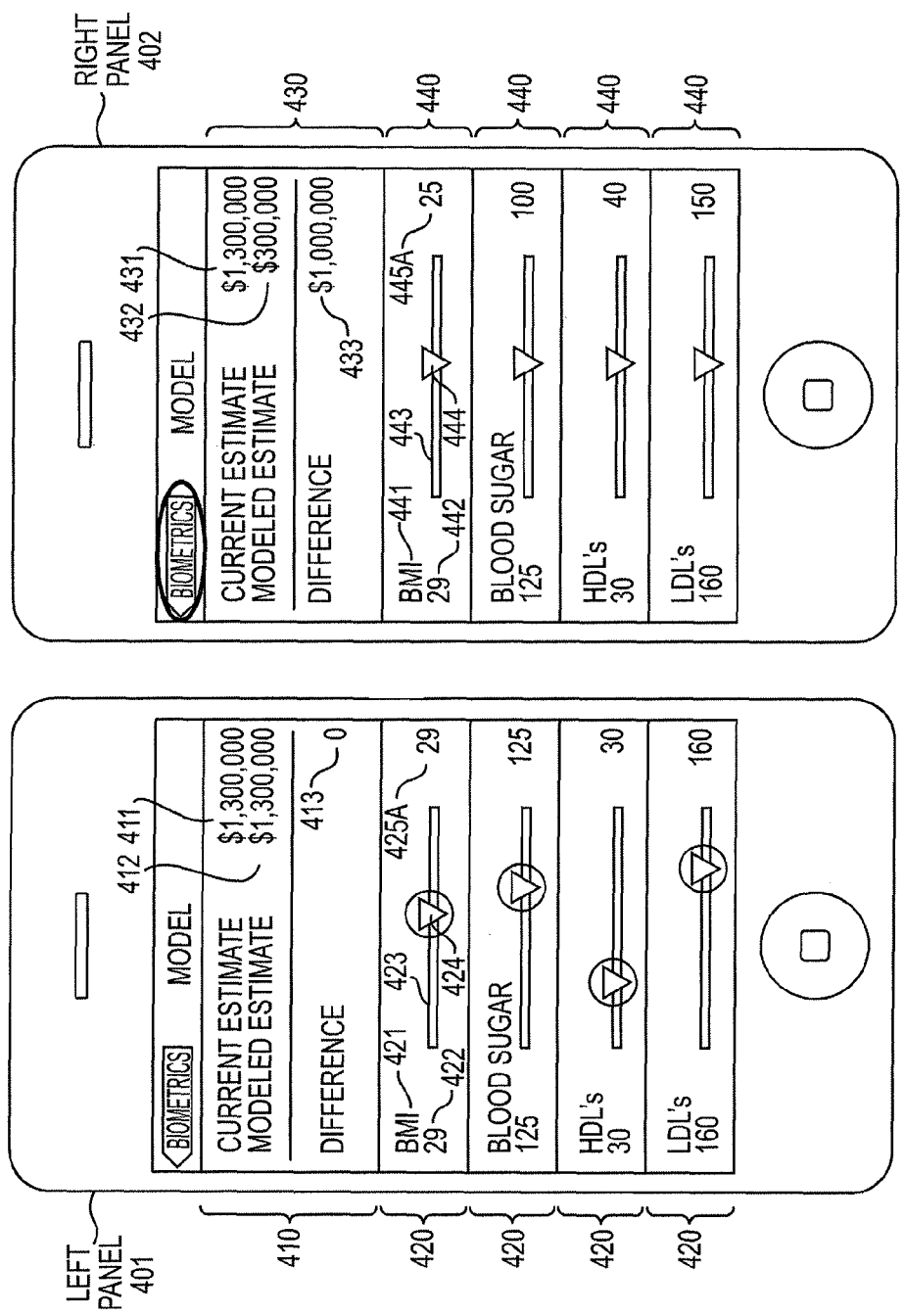
FIGS. 4A-4B illustrate a user interface for use by a member according to exemplary embodiments of the present disclosure.
Figure 4B:
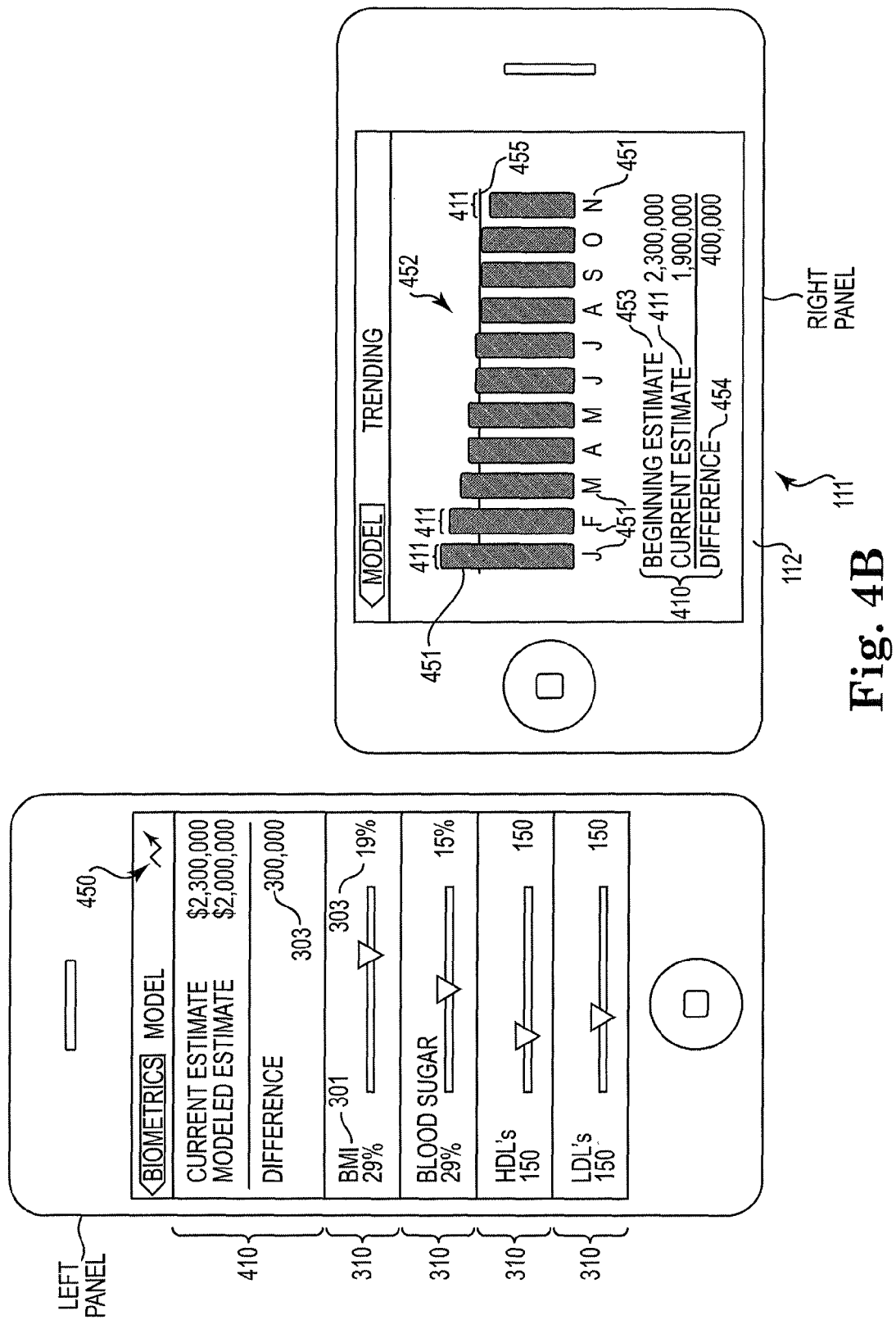

At a step 231, the member 101 can select, and the system 100 can present, that part of the user interface 112 with respect to biometrics, as further described with respect to FIG. 3B, FIG. 4A, and FIG. 4B.

After performing this step, the method 200 continues with the flow point 220.

At a step 232, the member 101 can select, and the system 100 can present, that part of the user interface 112 with respect to health and wellness.

After performing this step, the method 200 continues with the flow point 220.

At a step 233, the member 101 can select, and the system 100 can present, that part of the user interface 112 with respect to rewards.

As described herein, the member 101 can earn rewards "points" for actions that are clearly verifiable, and the member 101 can earn rewards "miles" for actions that are not clearly verifiable. Rewards "points" are generally more valuable than rewards "miles", and are exchangeable for things with more tangible value. For example, when rewards include money (cash payments, rebates of co-pays, reduced insurance rates, reduced co-pay requirements, or otherwise), they generally require rewards "points". When rewards "miles" are exchanged for rewards, they generally are exchangeable only for less-valuable rewards, such as coupons for discounted goods or services, "buy one get one free" deals, lottery tickets, a chance to win a new car, "perks" (such as a good parking spot), or recognition (such as an award or an announcement of the member's achievement). Methods for identifying actions for completion that may be eligible for rewards and granting such rewards are described further with respect to FIG. 2B.

As described herein, rewards can also include consumer goods (such as a free iPad™, a free cell phone, free airline tickets, free sport event tickets), consumer supplies (such as a "year's supply of" some product), or any other thing of value.

After performing this step, the method 200 continues with the flow point 220.

At a step 234, the member 101 can select, and the system 100 can present, that part of the user interface 112 with respect to alerts.

Alerts are described in further detail with respect to FIG. 3A.

After performing this step, the method 200 continues with the flow point 220.

At a step 235, the member 101 can select, and the system 100 can present, that part of the user interface 112 with respect to advice.

Advice messages are described in further detail with respect to FIG. 3A.

After performing this step, the method 200 continues with the flow point 220.

At a step 236, the member 101 can select, and the system 100 can present, that part of the user interface 112 with respect to long-term programs, as further described with respect to FIG. 5.

After performing this step, the method 200 continues with the flow point 220.

A flow point 200B indicates an end of the method 200. The method 200 repeats when the member 101 re-triggers it. Alternatively, the method 200 may repeat until some selected condition occurs.

In one embodiment, the system 100 includes a relatively large set of rules, such as at the database/analysis system 140, that convert information about the member 101 into possible requests for action by the member 101, the payer 102, or one or more providers 103. These requests for action can take the form of alerts/advice, or can take the form of chart notes with respect to the member 101, or otherwise. Thus, the overview and member interaction with the system in steps 212 and 220 may involve the system 100 executing various functions to provide the member with meaningful information to improve the health of the member.

In one embodiment, the system's rules are responsive to information the system 100 can collect about the member 101, possibly from disparate sources. The system 100 can collect information from reports of insurance and flexible spending account (FSA) claims, as these can indicate medical conditions or mental health conditions that might apply to the member 101. The system 100 can collect information from reports, as these can also indicate medical conditions or mental health conditions that might apply to the member 101. Reports can include those from medical personnel, laboratory technicians, physical therapists, mental health professionals, and other therapists.

In one embodiment, the system 100 can also collect health-related member information such as medical, provider, pharmaceutical, and eligibility information with respect to a member of a health plan. The information may include pre-adjudicated medical claims, pharmacy claims, clinical data such as electronic medical records ("EMRs") and HL7 messages, and/or member eligibility information such as demographics information including age, gender, health status. The information may be obtained from providers, pharmacists, biometric devices, self-reports by members and health insurance companies. Providers such as doctors and hospitals may supply a member's medical information to the system 100. For example, information with respect to visits and procedures, chart notes, observations and diagnoses, and otherwise may be supplied. Laboratory technicians can supply information with respect to laboratory visits and procedures, chart notes, laboratory observations and diagnoses, and otherwise. Physical therapists and other professionals can supply information with respect to visits and procedures, and measurements. Providers may also supply information about the provider itself such as provider ratings, costs and scheduling. Pharmacists can supply information with respect to filled prescriptions (but cannot assure that the filled prescription doses were actually taken). Similarly, biometric devices can supply relatively reliable information about the member 101, but only when they are used, and used correctly. They can measure blood pressure, cholesterol, glucose level, weight, and other facts. Health insurance companies may provide information related to a member's health plan, eligibility, annual deductibles, annual out-of-pocket amounts, accrued deductibles and out-of-pocket amounts and so on. Similarly, actions by members 101 generate information, at least in the sense that when members 101 express preferences, they provide information about their values and measures of importance. When members 101 self-report about their activities, the frequency and reliability of their reports provides information about their degree of interest. For example, when members set goals (e.g., intermediate goals, long-term goals), they express preferences (as to what to do, and how hard to work on it), and they provide information about their degree of interest.

The rules the system 100 applies can include medical rules; for example, rules derived from evidence-based medicine can help providers 103 maintain best practices. The rules the system 100 applies can also include business rules; for example, the payer might wish to encourage specific positive behaviors. And the rules the system 100 applies can also include rules of inference derived from statistical implications or from domain knowledge.

Figure 2B:
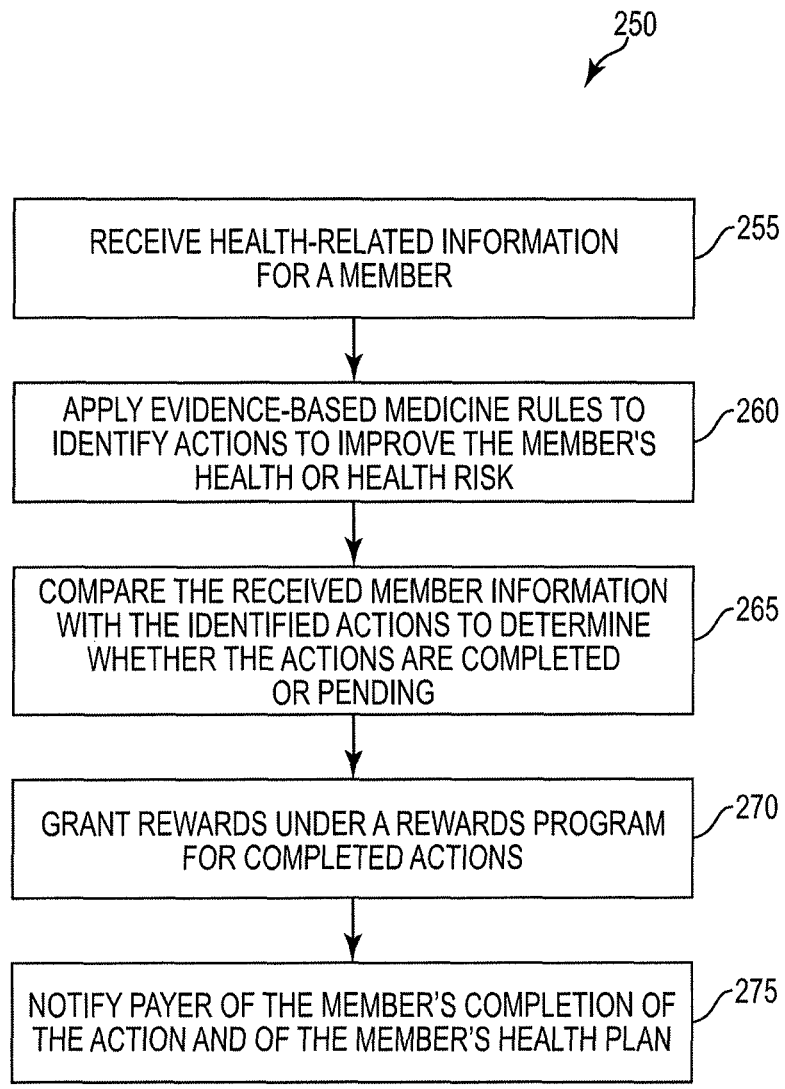
FIG. 2B shows a flow diagram of a method for granting rewards under a rewards program according to exemplary embodiments of the present disclosure.

FIG. 2B shows a flow diagram of a method 250 of encouraging healthy behavior by providing healthcare incentives according to the present disclosure. Method 250 may be performed by system 100 according to exemplary embodiments of the present disclosure. In method 250, the system 100 receives health-related information for the member in operation 255. As described herein, health-related information may include but is not limited to medical, provider, pharmaceutical, and eligibility information with respect to a member of a health plan. The information may be obtained from providers, pharmacists, biometric devices, self-reports by members and health insurance companies.

The method proceeds to operation 260 where evidence-based medicine rules are applied to the received member information to identify one or more actions to improve the member's health or health risk. The evidence-based medicine rules may be associated with identifying member gaps in care. For example, analysis against a set of predefined business rules may identify a group of healthcare services generally recommended for the member, e.g., a general set of gaps in care. The group of services recommended may be based on evaluating the member's healthcare plan eligibility, historic claims data, recently adjudicated medical claim data, recently adjudicated medication prescription claim data, and/or recent laboratory procedure data to identify services recommended for the member. Determining member healthcare plan eligibility may involve identifying the services for which the member qualifies under their healthcare plan. Historic claims data may be claims data from the past two to ten years. Member data that is recently adjudicated, such as recently adjudicated medical, prescription and laboratory procedure data, may be a set of data that is received from a data storage device on a periodic basis, such as weekly, bi-weekly or monthly. This information may be monthly aggregations of claims data extracted from a data warehouse. Identification of healthcare services recommended for the member, also referred to as gaps in member care, is discussed in a co-pending application having at least one common inventor having the Ser. No. 14/086,714, entitled "System, Method and Computer Program Product for Administering Consumer Care Initiatives," and filed on Nov. 21, 2013, the content of which is incorporated by reference in its entirety for any useful purpose. Currently, 17 HEDIS measures with over 580 rules may be used to analyze member claim data to identify gaps in care and determine whether the member is eligible to receive services for closing the gap in care. In this example, the rules may be run for each member, and the measures may be aggregated by health plan, which may enable the payer to identify members to target to incent activities to improve their health and health plan rating.

Method 250 continues by comparing the received member information with the identified one or more actions to determine whether the one or more actions are completed or pending in operation 265. The comparison identifies, for example, whether the member's previous actions result in completion of a recommended action and thus closed a gap in care that otherwise would be an open action (e.g., an open gap in care). For example, where the member is eligible for an annual physical identified in operation 260, comparison of the received member information, such as member claims data, may indicate the member has not yet received their annual physical. In this case, the member may be presented with information about completion of their annual physical such as links to providers offering these services. For example, the member may be alerted about the one or more actions to as they engage with the user interface of system 100. The actions may be classified as closures in gaps in care and may be considered HEDIS-based measures, accountable care organization ("ACO") measures, Medicaid guidelines, patient-centered medical home ("PCMH") measures, health plan-specific measures, employer-specific measures, Medicare risk-based measures or Medicare quality measures, which the member may engage in to improve their health or health risk. In addition, a payer, provider or third party may receive these completed or pending actions and may monitor the member's health or health risk. In some cases, the monitoring party may incent the member to engage in specific recommended action. In a particular example, the payer may incent the member to engage in an activity that will close a gap in the member's care, which may facilitate the payer in improving the quality rating of their health plan. In the aforementioned example, the action of receiving an annual physical may be a step in a rewards program described herein, the completion of which may result in the member being granted rewards.

In exemplary embodiments, the completed actions may be those that are verifiable, such as completion of a scheduled appointment with a provider, undergoing a lab procedure, refilling a prescription, and so on. In other exemplary embodiments, completed actions may be non-verifiable, such as self-reported actions. Such actions may be the member's reporting of self-weighing, exercise, and dieting. In yet other cases, completed actions may be temporarily non-verifiable but ultimately verifiable. These actions may include reported actions by the member or a provider where the action has not yet been verified by a secondary source of information. For example, where a provider or a member reports that the member has received a prescription for a medication, the system may associate a member-reported action of filling a prescription as temporarily non-verifiable until this action is verified using a pharmacy claim. The secondary source of information may be a party that regularly provides verifiable information and may include, but is not limited to: providers, laboratories, pharmacies and so on.

In operation 270, rewards under a rewards program are granted for completed actions, such as completion of an annual physical by the member. As described in more detail in connection with FIGS. 3A, 3B, 4A, 4B and 5, the rewards program generally includes a sequence of steps associated with actions that may be taken by the member to receive a reward under the program. The actions may include but are not limited to those actions that may help improve the health or health risk of the member. Each of the steps may be associated a reward, e.g., points, miles or other reward. The series of steps may be associated with both verifiable (e.g., medical claims data, pharmacy claims data, laboratory data) and non-verifiable actions (e.g., self-reported data) which may include both non-verifiable and temporarily non-verifiable actions. Because the comparison involves using verifiable and non-verifiable member data, the system 100 may grant rewards differently based on whether the action is verifiable.

For verifiable actions, prior to granting rewards, completion of the action may be verified based on the system 100 receiving information that confirms or denies completion of the action. For example, medical information for the member may be obtained from a medical provider that confirms or denies the completion of the action. In addition or alternatively, medical provider information may be obtained from a third party, such as a payer, that confirms or denies completion of the action. In addition or alternatively, biometric data may be obtained from authenticated devices that confirms or denies completion of the action by the member. For non-verifiable actions, self-reported member data may satisfy completion of the action as verification from a secondary source may be unavailable. Where the action is temporarily non-verifiable, actions associated with the self-reported member data are verified using a secondary source, for example, that regularly provides verifiable data. Rewards are granted in operation 270 based on whether the completed action is verifiable or non-verifiable. For completed verifiable action, the level of reward granted may be a first level of reward, while completed non-verifiable actions may be granted a second level of reward having a lesser value relative to the first. In addition or alternatively, verifiable actions may be associated with points, while non-verifiable actions may be associated with miles, and points may have a higher relative value compared to miles. As provided herein, accumulation of rewards, points and/or miles may allow the member to surrender these in exchange for things of value. In some implementations, where the rewards program is administered by a payer, the rewards for completion of actions associated with gap closures that can help improve a health plan's star rating, quality rating and/or financial performance may have a higher relative value compared to other actions.

In operation 275 a payer may be notified of the member's completion of the action and of the member's health plan. This notification enables a payer, such as a health insurance company, to be updated on the activities of the member and on the effectiveness of the rewards program in incenting their members to engage in activities that can improve member health as well as the health plan. Providers using the system may therefore track performance of quality measures under the health plan of the member.

Healthcare Incentive User Interface

Overview Presentation.

FIGS. 3A and 3B illustrate a user interface that may be provided according to exemplary embodiments of the present disclosure.

FIG. 3A shows the user interface 112, including an overview, as shown at the user workstation 110 on its screen 111.

The overview includes a set of elements 300, each element 300 being presented on the screen 111. In one embodiment, each element 310 can include a title 301 and sub-title 302, a summary presentation 303, and a detail button 304.

A first element 310 includes a summary of the member's biometrics information. Its title 301 can include the word "Biometrics". Its sub-title 302 can include the phrase "In Goal Range". Its summary presentation 303 can include an indicator of how many or which biometrics values for the member 101 are within their goal range. In this particular case, the summary presentation 303 includes the term "17%", or approximately one value out of six; in alternative embodiments, the summary presentation 303 for biometrics can indicate which ones of the biometrics values for the member 101 are within their goal range. Its detail button 304 includes a rightward-pointing chevron, which when triggered changes the screen 111 to show the member's actual biometrics values.

A second element 310 includes a summary of the member's health and wellness information. Its title 301 can include the phrase "Health & Wellness". Its sub-title 302 can be blank. Its summary presentation 303 can include one indicator of how many calories worth of exercise the member 101 has performed for the day, expressed as a bar graph labeled "Exercise", and one indicator of how many calories worth of food the member 101 has consumed for the day, expressed as a bar graph labeled "Diet". In this particular case, the element 300 does not include a summary presentation 303 or a detail button 304.

A third element 310 includes a summary of the member's rewards points. Its title 301 can include the word "Rewards". Its sub-title 302 can be blank. Its summary presentation 303 can include a numerical value of the number of rewards "points" and "miles" the member 101 has earned, and a bar graph showing an approximate magnitude, optionally relative to a number of rewards points the member 101 could have earned by this time. In this particular case, the member 101 has earned several rewards points, and the bar graph shows that this is about 40% of the number of rewards points the member 101 could have earned by this time. Its detail button 304 includes a rightward-pointing chevron, which when triggered changes the screen 111 to show the member's actual rewards points values (not shown).

As described herein, rewards "points" are earned by the member 101 by conducting health-related activities that can be clearly confirmed, such as attending a meeting with a health coach, or having a weight measure confirmed at an office visit or physical therapy session. As described herein, the member 101 earns rewards "miles" by conducting health-related activities that can only be confirmed with room for error, such as a self-report that the member 101 ran for 30 minutes today, or filled a prescription for prescribed medication. In the latter case, filling the prescription and pickup from the pharmacy can be clearly confirmed, but whether the member 101 actually took the medication cannot be clearly confirmed. Rewards "points" are more valuable than rewards "miles" when the member 101 wishes to redeem them for actual rewards. In some implementations, points may be associated with both verifiable and non-verifiable actions. Verifiable actions may be associated with relatively more points compared to those that are non-verifiable.

A fourth element 310 includes a summary of the member's pending alerts. Its title 301 can include the word "Alerts". Its sub-title 302 can include either the phrase "You have alerts" or the phrase "You do not have alerts", or some variant thereof. Its summary presentation 303 can include a box with a number of alerts shown therein; in alternative embodiments, the summary presentation 303 for alerts can be colored to show alerts more blatantly than just a number. For example, the summary presentation 303 can be green for no alerts, yellow for one alert, and red for two or more alerts, or any alerts that are marked urgent. In this particular case, the summary presentation 303 for alerts includes the number "2", indicating two pending alerts. Its detail button 304 includes a rightward-pointing chevron, which when triggered changes the screen 111 to show the actual text of the member's alerts (not shown).

A fifth element 310 includes a summary of the member's pending advice messages. Its title 301 can include the word "Advice". Its sub-title 302 can include either the phrase "You have advice" or the phrase "You do not have advice", or some variant thereof. Its summary presentation 303 can include a box with a number of advice messages shown therein; in alternative embodiments, the summary presentation 303 for advice can be colored to show advice more blatantly than just a number. For example, the summary presentation 303 can be green for no advice messages, yellow for one advice message, and red for two or more advice messages, or any advice messages that are marked urgent. In this particular case, the summary presentation 303 for advice includes the number "1", indicating one pending advice message. Its detail button 304 includes a rightward-pointing chevron, which when triggered changes the screen 111 to show the actual text of the member's advice messages (not shown).

As described herein, in one embodiment, the member 101 can receive advice/alerts from the payer workstation or the provider workstation 130. For example, the member 101 can receive advice/alerts by having them displayed at the user interface 112, by forwarding them to the member's email address, by directing them (possibly wirelessly) to a nearby printer, by playing a synthesized voice reading of the advice/alerts, or otherwise. The system 100 notes which advice/alerts the member 101 receives, and by what media, with the effect that the system 100 can later determine how effective any one advice/alert is in prompting action by the user, after accounting for frequency, importance, and urgency.

In one embodiment, advice/alerts can be tailored to the particular member 101 and the medical issues being engaged by the particular member 101. For example, the system 100 can determine, in response to the member's biometric information, as well as age and gender, office visits, prescriptions, and otherwise, whether the member 101 is at risk for a heart problem.

Advice can include information of interest to the particular member 101, not based on any particular event, but tailored to the particular member 101, such as in response to which advice they have read in more detail than just the headline. For example, advice can include heart-healthy recipes, suggestions for exercise activities that might be of interest to the member, suggestions on how to spend less on medications, and otherwise. If the particular member 101 does not read recipes, the system 100 can send other types of advice instead, such as suggestions on how to eat healthy meals while traveling.

Alerts can include information that is time sensitive, such as a reminder to schedule a follow-up to the member's most recent office visit. In such cases, the alert can include a user interface element, such as a pop-up or a screen, aiding the member 101 in scheduling the office visit from the user workstation 110 in response to the alert. Depending on their importance, alerts can be tailored to demand the member's attention (without getting ignored for being obnoxious). For example, alerts can also include a reminder to attend a scheduled office visit, a reminder to fill a particular prescription, and a reminder to take that prescription when scheduled. Alerts can also indicate how many "points" or "miles" the member 101 earns by taking each alerted action.

A sixth element 310 includes a summary of the member's engagement with care programs such as long-term programs that the member engages in over time with the goal of improving health or health risk. Its title 301 can include the word "Programs". Its sub-title 302 can include the word "Engagement", or some variant thereof. Its summary presentation 303 can include an indicator of how many or which care programs the member 101 is actively engaged with. In this particular case, the indicator shows "0%", that is, that the member 101 is not engaged with any care programs. Its detail button 304 includes a rightward-pointing chevron, which when triggered changes the screen 111 to show the actual programs a member may be engaged in (not shown).

As described herein, in one embodiment, the member 101 can elect one or more care health programs offered by the system 100 and in particular to the member 101. There might be more than one such program available for the member 101, and it is the member 101 who decides which program (if any) they engage in. For example, if the system 100 has concluded that the member 101 is at risk both for a heart problem and for developing diabetes, in response to their BMI value, their blood sugar measurement, and their blood pressure measurement, the system 100 can (in response to one or more medical rules) suggest that the member 101 engage in care programs for diabetes and for hypertension. The member 101 can choose to engage in one or more such programs, and the system 100 can determine a measure of enthusiasm for each program that the member 101 exhibits by their actions.

FIG. 3B shows the user interface 112, including the member's biometrics information, as shown at the user workstation 110 on its screen 111 shown in FIG. 3A.

Similar to the elements 310 in FIG. 3A, each element 320 in FIG. 3B includes a summary of one selected biometrics measure, and can include a similar title 301, sub-title 302, summary presentation 303, and detail button 304. In each such element 320 in FIG. 3B, its title 301 can include the name of the biometrics measure. In the first particular case, its title 301 can include the name "BMI". Its sub-title 302 can include the phrase "Above Goal Range". Its summary presentation 303 can include an indicator of what value the member's BMI has. In this particular case, the summary presentation 303 includes the value "29", or a BMI value that is somewhat overweight in alternative embodiments, the summary presentation 303 for biometrics can include a slider or some other indicator regarding those biometrics values for the member 101. Its detail button 304 includes a rightward-pointing chevron, which when triggered changes the screen 111 to show further detail about the member's biometrics value, in this case, the member's BMI.

In this particular case, the selected biometrics measures for the member 101 are "BMI", which is above goal range with a (dimensionless) value of 29, "Blood Sugar", which is above goal range with a value of 125 mg/dL, "HDL's" (a cholesterol measure), which is in goal range with a value of 30 mg/dL, "LDL's" (another cholesterol measure), which is in goal range with a value of 160 mg/dL, "Triglycerides", which is in goal range with a value of 150 mg/dL, and "Blood Pressure", which is above goal range with a (systolic) value of 210 mmHg.

Biometrics Cost Estimate.

FIGS. 4A-4B illustrate user interfaces according to exemplary embodiments of the present disclosure.

A biometrics cost estimate model can include a first element 401 of the user interface 112 of the member workstation 110, shown in the left-hand panel of FIG. 4A. In that first element, a first biometrics cost estimate 410 is presented, along with a first set of biometrics elements 420.

The first biometrics cost estimate 410 can include a current estimate 411, a modeled estimate 412, and a difference 413 (the latter calculated as current estimate 411 minus modeled estimate 412). The current estimate 411 is calculated from actuarial tables or lifetime cost curves in response to the current values of the member's information, e.g., biometric measures, conditions, age gender and/or diseases, if available or present. The modeled estimate 412 is also calculated from actuarial tables or curves, in response to a set of slider values of the member's biometric measures that may be selected by a user. This has the effect of showing the member 101 how much healthcare cost saving can be achieved over the member's lifetime or another time period by taking action to alter the current values of the member's biometric measures to reach the slider values of the member's biometric measures.

In the left-hand panel of FIG. 4A, the first set of biometrics elements 420 can include selected ones of the member's biometric measures. Each such element 420 includes a title 421, an actual value 422, a slider bar 423 showing a scaled relative value with a slider 424 positioned thereon, and a first model value 425A. When the first model value 425A equals the actual value 422, the slider 424 is circled to so indicate.

In this particular case, the member 101 has a BMI of 29, a Blood Sugar measure of 125 mg/dL, an HDL's measure of 30 mg/dL, and an LDL's measure of 160 mg/dL. The current estimate 411 is $1,300,000 in lifetime predicted healthcare costs for the member 101, in response to these current values. The slider 424 has the first slider value 425A equal to the actual value 422 in all cases, so the modeled estimate 412 is the same as the current estimate 411, that is, also $1,300,000 in lifetime predicted healthcare costs for the member 101, in response to these modeled values. The calculated difference 413 is zero.

The biometrics cost estimate model can also include a second element 402 of the user interface 112 of the member workstation 110, shown in the right-hand panel of FIG. 4A. In that second element, a second biometrics cost estimate 430 is presented, along with a second set of biometrics elements 440.

The second biometrics cost estimate 430 can include a current estimate 431, a modeled estimate 432, and a difference 433 (the latter calculated as current estimate 431 minus modeled estimate 432). The current estimate 431 is calculated from actuarial tables in response to the current values of the member's biometric measures, and so should be the same as the current estimate 411 in the first biometrics cost estimate 410. The modeled estimate 432 is also calculated from actuarial tables, but in response to the goal values of the member's biometric measures. This has the effect of showing the member 101 how much healthcare cost saving can be achieved by taking action to alter the current values of the member's biometric measures to reach the goal values of the member's biometric measures.

In the right-hand panel of FIG. 4A, the second set of biometrics elements 440 can include selected ones of the member's biometric measures. Each such element 440 includes a title 441, an actual value 442, a slider bar 443 showing a scaled relative value with a slider 444 positioned thereon, and a second model value 445A.

In this particular case, the member 101 has elected a goal BMI of 25, a goal Blood Sugar measure of 100 mg/dL, a goal HDL's measure of 40 mg/dL, and a goal LDL's measure of 150 mg/dL. The current estimate 411 is $1,300,000 in lifetime predicted healthcare costs for the member 101, in response to the member's current values (as shown in the left-hand panel). The slider 444 has the second model value 445A equal to the goal value in all cases, so the modeled estimate 412 is what would be estimated if the member 101 reached those goal values. In this particular case, the modeled estimate is $300,000, which is $1,000,000 less than the current estimate 411, in response to these model values. The calculated difference 413 is therefore $1,000,000; the member 101 can save $1,000,000 in healthcare cost by taking action to alter the current values of the member's biometric measures to reach the goal values of the member's biometric measures. The payer 102 hopes this large dollar amount is sufficient to motivate the member 101.

FIG. 4B (collectively including a left-hand panel and a right-hand panel) shows a user interface according to exemplary embodiments of the present disclosure.

Similar to FIG. 3B, FIG. 4B, left-hand panel, shows the current biometrics measures for the member 101 with biometrics titles 301 and summary presentations 303, and additionally, the first biometrics cost estimate 410.

FIG. 4B, left-hand panel, also shows a trend button 450, which transfers the user interface 112 to a state in which it shows trend estimates 451 from each calculated past current estimate 411 from FIG. 4A, once per month. This has the effect that the member 101 can see in graphical form the decrease (or increase) in estimated lifetime healthcare cost as the member 101 takes action to alter their biometrics measures.

FIG. 4B, right-hand panel, shows the trend information in graphical form, as described above. The user interface 112 can include a screen 111, showing a separate current estimate 411 from FIG. 4A, computed once per month, that is, the trend estimates 451, presented in a bar graph 452. Below the bar graph 452, the user interface 112 can include a beginning estimate 453, that is, the earliest of the trend estimates 451, shown numerically and derived from cost curves and based on the earliest member information available, and a current estimate 411, that is, the most recent of the trend estimates 451, also shown numerically, and their difference 454. This has the effect that the member 101 can see in graphical form the decrease (or increase) in estimated lifetime healthcare cost as the member 101 takes action to alter their biometrics measures. In this particular case, the member's beginning estimate 453 is $2,300,000, their current estimate 411 is $1,900,000, and the difference 454 is $400,000, which corresponds to the November trend estimate 451 in the bar graph 452. As shown in FIG. 4B, right-hand panel, the member's trend estimates may be compared to a peer cost average baseline 455 and may enable the member to understand how their projected healthcare costs compare others similarly situated.

According to certain embodiments, the completion of actions in the member's rewards program may result in a change to a current estimate 411. For example, the completion of such actions may or may not affect the member's current biometrics, but may correlate to a reduction in the member's current estimate 411. In a further example, the completion of such actions may positively affect the member's health-related information and may be indicative an improvement of the member's heath or health risk, which may be correlated to actuarial tables or curves.

Although the cost estimates and cost savings estimates provided herein are lifetime estimates, lifetime estimates are exemplary, and embodiments of the present disclosure may provide estimates for other timeframes such as multi-year, annual, bi-annual, monthly and weekly timeframes. Such estimates may be based on the member's information as described above and may be determined in relation to actuarial tables or curves.

Example Rewards Programs.

Figure 5A:
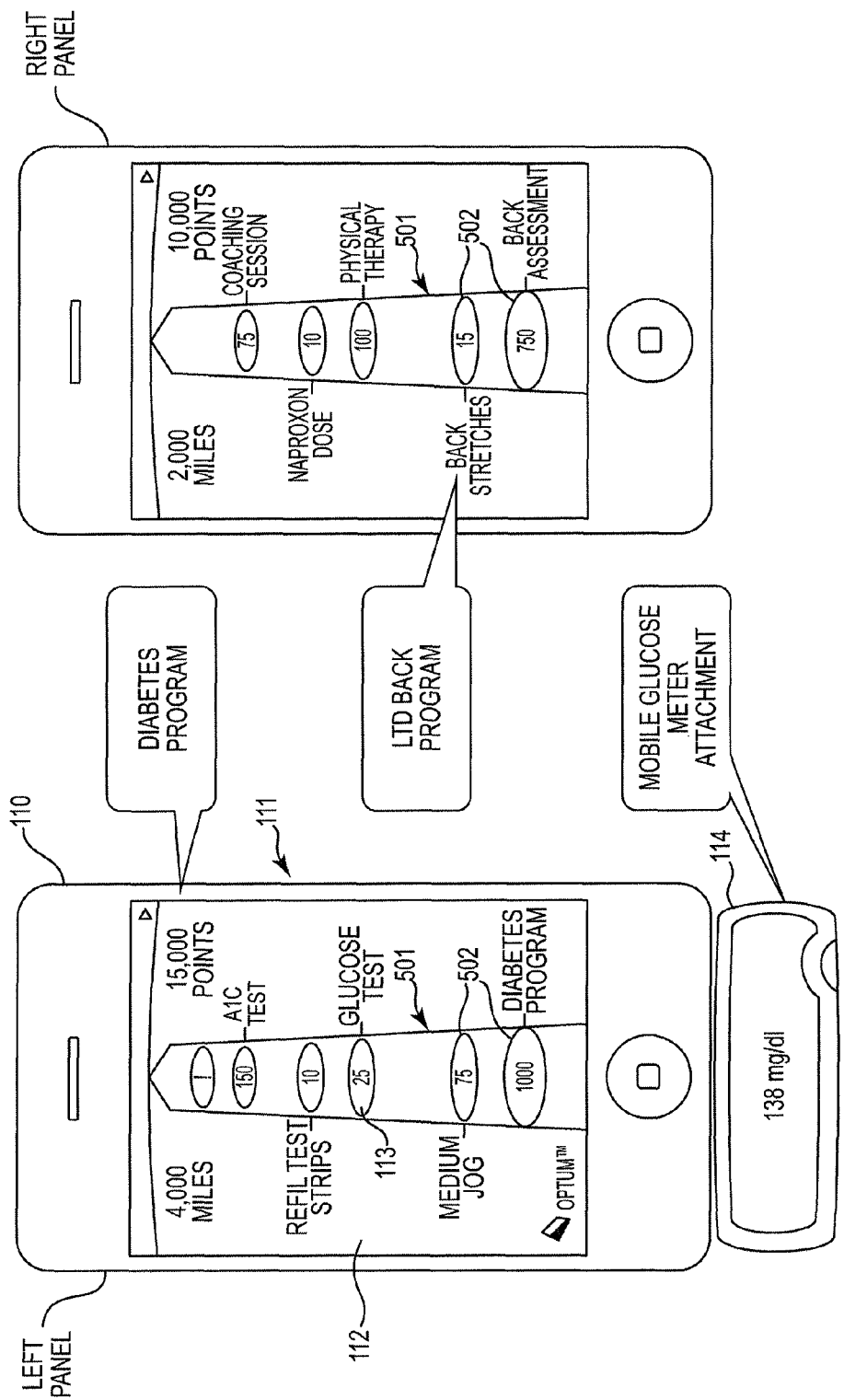
FIGS. 5A-5B illustrates a user interface for use by a member according to exemplary embodiments of the present disclosure.
Figure 5B:
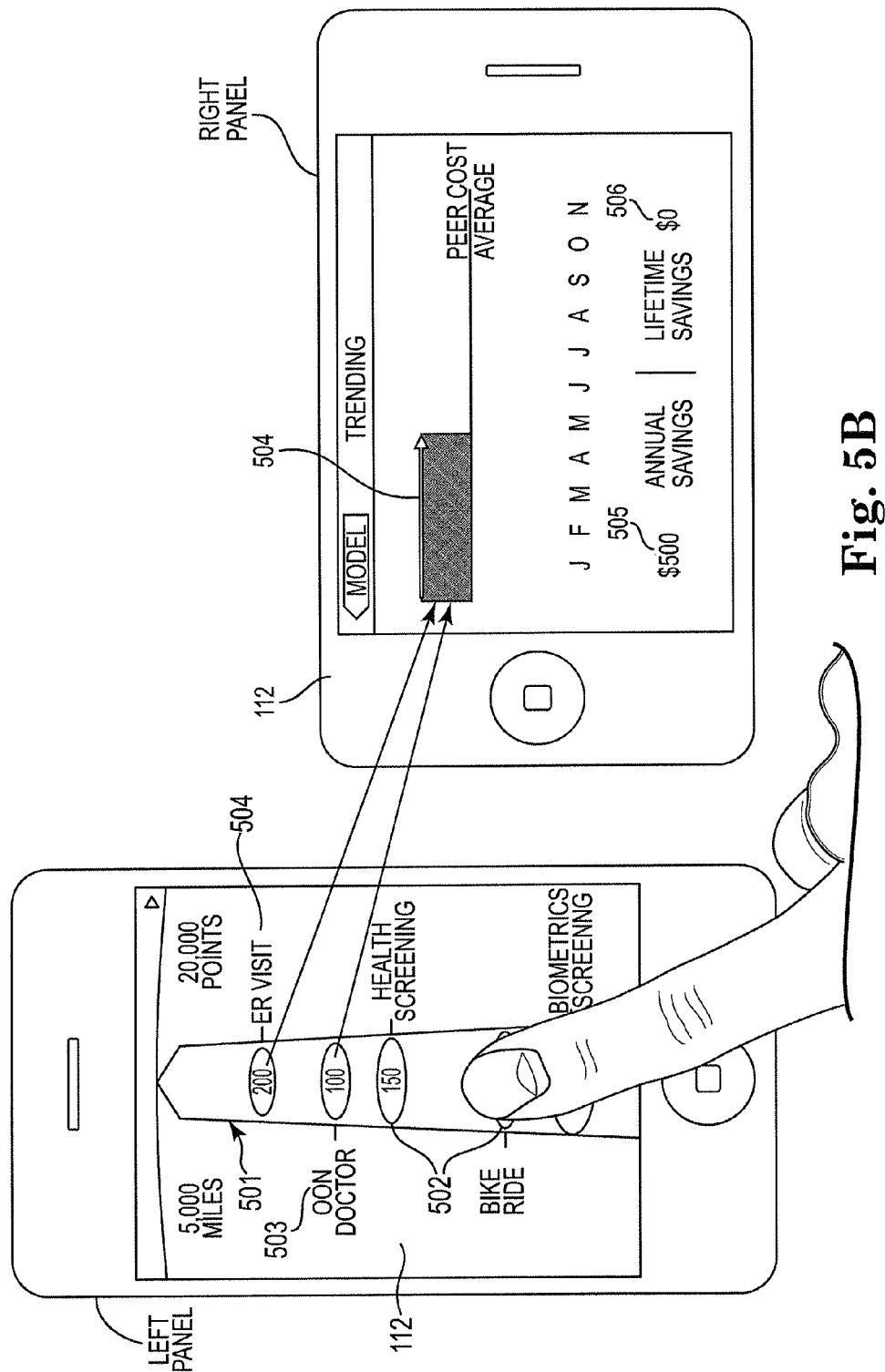

FIGS. 5A and 5B (each collectively including a left-hand panel and a right-hand panel) show a user interface 112 for displaying a member's alerts and tracking a member's rewards according to exemplary embodiments of the present disclosure. The alerts and corresponding rewards may be displayed for open alerts. The user interface 112 may be displayed when a user logs in to their account and the user has an active or open alert for a measure to be completed under their rewards program. Where the user does not have active or open alerts, the user may be directed to the user interface of FIG. 3A instead.

FIG. 5A, left-hand panel, shows a user interface 112 scenario for alerts and rewards for a diabetic member. Where the member's information indicates the member is experiencing diabetes and hypertension, for example, the alerts and rewards programs for addressing each of diabetes and hypertension may be provided on a common interface.

Further, where the member's information indicates the member is interested in engaging in a health and wellness program, e.g., such as jogging, and is experiencing one or more health conditions, the alerts and rewards diagnosis-related programs as well as a health and wellness program may be presented on a common interface. The alerts and rewards can include a pathway 501, on which there can be a sequence of actions 502 to be performed by the member 101. A "points" value or "miles" value can be associated with each action 502. This has the effect that the member 101 can see the planned sequence of actions, their order, an approximate timing (perceived distance on the path can act as a proxy for time delay), and a reward value for each action. For example, in the panel, the member 101 can see that entering a diabetes program, as a verifiable step, has a reward value of 1,000 points, going on a medium jog, as a non-verifiable step, has a reward value of 75 miles, and taking a glucose test, as either a verifiable or a non-verifiable step depending on whether the biometrics device is authenticated, has a reward value of 25 points when the test is verifiable and has a rewards value of miles when the test is not verifiable.

As described herein, "points" are earned for actions that the system 100 can clearly verify (such as those conducted with an external party, such as a provider 103), while "miles" are earned for actions that the system 100 cannot clearly verify (such as those that are self-reported, or for which the external party can only partly verify the action). For example, joining a diabetes program has reward points instead of reward miles, because the action includes attending meetings of the program participants, and the provider 103 can verify attendance. In contrast, a medium jog is self-reported by the member 101; the system 100 cannot ask any provider 103 for verification, unless the member 101 were to jog at the provider's location (such as if the provider 103 were a physical therapist at a location with a jogging track).

As described herein, reward points are "worth" more than reward miles, at least in the sense that reward points are generally associated with more clearly valuable, and more valuable, rewards, such as monetary rebates and free consumer goods. Reward miles are generally only associated with less clearly valuable, and less valuable, rewards, such as coupons for lower prices, and "perks" at work, such as a good parking spot. Of course, each member 101 might value each reward differently. This has the effect that some rewards available in exchange for reward miles might be more motivating to one or more members 101 than other rewards available in exchange for reward points. This does not pose a problem, as the system 100 is intended to offer disparate rewards in the hope that one or more of them would be valuable enough to attract members 101 to reduce their healthcare costs. Although the description addresses rewards in the context of points and miles, this context is exemplary and various types of rewards may be provided such as monetary accumulations (e.g., dollars), points accumulations and/or miles accumulations, where the different types of rewards have different relative values.

Taking a glucose test may, for example, only earn reward miles if the test were self-reported and not verifiable using an authenticated biometrics device. The figure shows, at the left-hand panel, that the user workstation 110 can have a peripheral device 114 coupled thereto. The peripheral device 114 can be an authenticated device and may measure glucose level and report its measurement to the system 100, with the effect that the peripheral device 114 can verify that the member 101 conducted a glucose test. Thus, in this figure, rewards are valued as points.

FIG. 5A, right-hand panel, shows a user interface 112 for alerts and rewards for a member with a back injury. This second alerts and rewards scenario demonstrates use of a pathway 501, on which there can be a sequence of actions 502 to be performed by the member 101, with a "points" value or "miles" value that can be associated with each action 502. In the figure, the pathway 501 is shown to be straight, as if a roadmap were laid out in front of the member 101 and the pathway 501 was the best path to a particular destination. In the context of the invention, there is no particular requirement for any such limitation. In alternative embodiments, the pathway 501 may instead meander to and fro, optionally to present more actions on the pathway 501, or might even form a closed loop, optionally to present some actions as being prescribed for endless repetition.

The actions associated with the back injury management program can differ from the actions associated with the diabetes management program. This has the effect that members 101 with differing medical conditions can be alerted to take actions and offered rewards that can be matched to their particular medical conditions. This can be performed with the member's biometric measures, with the member's age and gender, with the member's history of reported ailments, and with the member's history of compliance with medical personnel's requests.

In one embodiment, the system receives self-reported member planned activities as input from the member to create at least one of the alerts and rewards instances. For example, the member may enter a health-related goal into the user interface of FIG. 4A. In this example, the member may set a goal for one or more of the member's biometrics such as BMI, blood sugar, HDLs, LDLs, triglycerides, blood pressure, resting heart rate and so on. In a further example, the member may set a goal for engaging in activities such as diet, exercise, taking and/or refilling prescriptions regularly. The member-entered goals may be used to generate alerts and rewards or any rewards or goal-oriented program of the present disclosure. The member may thus engage in the goal-oriented program having been customized according to the member's own goals.

In one embodiment, the system 100 can assign a measure of engagement to the degree to which the member 101 conducts the actions designated by the long-term rewards program. For example, a particular member 101 that only rarely performs verifiable actions, and only infrequently self-reports individual un-verified actions, might be determined by the system 100 to be relatively unmotivated to perform that particular long-term rewards program. This has the effect that the system 100 determines that the member 101 has a relatively low degree of engagement with that program.

In response to a relatively low degree of engagement, the system 100 might assign lesser rewards to less-engaged members 101, effectively requiring fuller participation to earn greater rewards. In contrast, the system 100 might assign greater rewards to less-engaged members 101, on the grounds that greater rewards are required to coax those members 101 into conducting the desired actions. Whether lesser rewards or greater rewards are superior is a question that can be left to the database/analysis system 140, which can aggregate the many examples, correct for demographic and other unrelated factors that might affect the statistics, and pronounce upon which is more likely to yield results. Furthermore, in some implementations, the members engagement in the system bay be under the rewards program, cost savings program, or both.

In one embodiment, the system 100 can display an amount of earned reward points assign a measure of engagement to the degree to which the member 101 conducts the actions designated by the long-term rewards program. For example, a particular member 101 that only rarely performs verifiable actions, and only infrequently self-reports individual un-verified actions, might be determined by the system 100 to be relatively unmotivated to perform that particular long-term rewards program. This has the effect that the system 100 determines that the member 101 has a relatively low degree of engagement with that program.

FIG. 5B, left-hand panel, shows a user interface 112 for tracking a member's alerts and rewards according to exemplary embodiments of the present disclosure. In this embodiment, the alerts and rewards may be associated with a member's selected goals and with alerting a member to actions that result in higher healthcare costs for the member. As with FIG. 5B, the rewards program can include a pathway 501, on which there can be a sequence of actions 502 to be performed by the member 101. Although the rewards program may be associated with miles and points as described herein, the pathway 501 may include alerts associated with high cost drivers. In this example, the pathway includes an alert for visiting an out-of-network doctor 503 and an emergency room visit 504 engaged in by the member. Each of these member activities, while potentially beneficial to the member to address the member's health and thus associated with miles and/or points, may be associated with higher costs including out-of-pocket and deductibles.

FIG. 5B, right-hand panel, shows a user interface 112 for tracking a member's trending financial impact for electing high cost drivers compared to average peer costs of other members within the network that may elect alternatives to the high cost drivers. The member's past healthcare and lifestyle activities may be used to calculate the member's projected healthcare costs 504. In FIG. 5B, the annual savings 505 of $500 may be realized by the member by electing lower cost alternatives to out-of-network doctor visits and emergency room visits, such as scheduled doctor visits within the member's network or an urgent care visit as opposed to an emergency room visit. Based on the member's subsequent healthcare activities, the user interface may display lifetime savings 506. In this example, the member's engagement in high cost drivers results in a lifetime savings of $0.

According to certain implementations, the rewards program may utilize the member's estimated cost savings as a driver in determining rewards values. Where a member is presented with actions within the rewards program that, when completed, results in cost savings or projected cost savings, the value of the reward may be relatively higher compared to completion of actions that are not associated with cost savings or are associated with a lesser cost savings. For example, receipt of a back assessment may result in a higher projected cost savings compared to cost savings associated with receiving physical therapy alone, and thus completion of a back assessment may result in an award of a relatively higher points value, e.g., 750 points in FIG. 5, right-hand panel, in relation to a points value for completing physical therapy, e.g., 100 points in FIG. 5, right-hand panel. In some cases, a rewards value may be determined based on how cost-effectively the member completed an action within the rewards program. For a member completing an annual checkup, the rewards value may differ based on whether the member completed a checkup from an in-network or an out-of-network provider. An annual checkup from an out-of-network provider may have a rewards value that is relatively less, e.g., 100 miles in FIG. 5B, left-hand panel, than a rewards value for completing the same service from an in-network provider, which may have a points value that generally is of more worth compared to miles, or may have a relatively higher miles value. Thus, the implementations may encourage the member to engage in both healthy and cost-effective actions in the rewards program.

According to further implementations, the rewards program may utilize a member's cost savings as the primary driver in encouraging the member to engage in healthy and cost-effective actions, and a rewards system with points and/or miles may not be included. In one exemplary embodiment, the user interface 112 may display a rewards program pathway with actions for the member to view, but points/miles values may not be displayed. In a further exemplary embodiment, the member's cost savings associated with a pending or completed action may be displayed. In yet a further exemplary embodiment, the member may be presented with information showing the trending financial impact as illustrated in FIGS. 4B and 5B as an alternative to an accumulation of points and/or miles. In still a further exemplary embodiment, accumulated cost savings for completing actions in the member's rewards program may result in awarding the member with a thing of value.

Alternative Embodiments

Elements of the system are described herein with respect to one or more possible embodiments, and are not intended to be limiting in any way. In the context of the invention, there is the particular requirement for any such limitations as described with respect to any elements of the system. For example, individual elements of the described apparatuses could be replaced with substitutes that perform similar functions. Moreover, as described herein, many individual elements of the described apparatuses are optional, and are not required for operation.

Although control elements of the one or more described apparatuses are described herein as being executed as if on a single computing device, in the context of the invention, there is no particular requirement for any such limitation. For example, the control elements of the one or more described apparatuses can include more than one computing device, not necessarily all similar, on which the element's functions are performed.

Certain aspects of the embodiments described in the present disclosure may be provided as a computer program product, or software, that may include, for example, a computer-readable storage medium or a non-transitory machine-readable medium having stored thereon instructions, which may be used to program a computer system (or other electronic devices) to perform a process according to the present disclosure. A non-transitory machine-readable medium includes any mechanism for storing information in a form (e.g., software, processing application) readable by a machine (e.g., a computer). The non-transitory machine-readable medium may take the form of, but is not limited to, a magnetic storage medium (e.g., floppy diskette, video cassette, and so on); optical storage medium (e.g., CD-ROM); magneto-optical storage medium; read only memory (ROM); random access memory (RAM); erasable programmable memory (e.g., EPROM and EEPROM); flash memory; and so on.

While the present disclosure has been described with reference to various embodiments, it will be understood that these embodiments are illustrative and that the scope of the disclosure is not limited to them. Many variations, modifications, additions, and improvements are possible. More generally, embodiments in accordance with the present disclosure have been described in the context of particular embodiments. Functionality may be separated or combined in procedures differently in various embodiments of the disclosure or described with different terminology. These and other variations, modifications, additions, and improvements may fall within the scope of the disclosure and the inventive subject matter.

The invention claimed is:

1. A computer-implemented method of encouraging healthy behavior, the method comprising the steps of:
    receiving, at a server, health-related member information with respect to a member of a health plan;
    applying evidence-based medicine rules to the received member information to identify actions to improve the member's health or health risk, wherein the actions may be pending or completed;
    comparing the received member information with the identified actions to determine whether the actions are completed; and
    for completed actions, granting rewards under a rewards program, the rewards program comprising a sequence of steps including at least one action that is verifiable and at least one action that is non-verifiable, each step in the sequence being associated with a reward;
    wherein granting rewards for the at least one verifiable action comprises verifying completion of the at least one verifiable action by obtaining biometric data from an authenticated biometric device that confirms or denies completion of the at least one verifiable action, wherein the biometric data comprises biometric data selected from the group consisting of blood pressure data, glucose level data, cholesterol data, and weight data, and wherein the authenticated biometric device reports one or more of blood pressure, glucose level, cholesterol, or weight;
    wherein granting rewards for the at least one non-verifiable action comprises receiving non-verifiable medical information or self-reported member data and the granted rewards for the at least one non-verifiable action are based thereon; and
    wherein the completed verified action is granted a first level of reward and the completed non-verifiable action is granted a second level of reward having a lesser value relative to the first.

2. The method of claim 1, further comprising, prior to granting rewards for self-reported member data, verifying actions associated with the self-reported member data are completed using member information received from a secondary source.

3. The method of claim 1, further comprising identifying open actions and presenting the open actions to the member on a user interface.

4. The method of claim 3, wherein
the step of presenting the user interface includes:
    presenting at least a portion of the sequence of steps under the rewards program, each step presented associated with rewards;
    receiving self-reported member planned activities as input from the member to create at least one of the steps; and
    receiving self-reported member data as input from the member with respect to activity with respect to the at least one of the steps.

5. The method of claim 1, wherein the health-related member information received with respect to the member comprises one or more of pre-adjudicated medical claims, pharmacy claims, adjudicated medical claims or clinical data.

6. The method of claim 5, wherein the clinical data received comprises clinical data received from provider systems including one or more of electronic medical records or HL7 messages.

7. The method of claim 1, wherein the one or more actions identified are HEDIS-based measures, accountable care organization ("ACO") measures, Medicaid guidelines, patient-centered medical home ("PCMH") measures, health plan-specific measures, employer-specific measures, Medicare risk-based measures or Medicare quality measures.

8. The method of claim 1, wherein the rewards can be accumulated and exchanged for items of value to the member.

9. The method of claim 8, further comprising:
    determining a degree to which the member is engaged in the rewards program; and
adjusting a level of reward in response to the degree to which the member is engaged.

10. The method of claim 1, further comprising tracking performance of quality measures under the health plan of the member.

11. The method of claim 1, further comprising notifying a payer of the completed action and of the health plan for the member.

12. The method of claim 1, further comprising:
    determining, in response to receiving said health-related information, a projected cost associated with said member; and
    determining, in response to identifying completed actions, a reduction in the projected cost.

13. The method of claim 12, wherein the identified completed actions comprise at least one change to the member's health-related information that is indicative of improving the member's health or health risk.

14. The method of claim 12, wherein the determined projected cost associated with said member is a lifetime cost based on actuarial cost curves.

15. The method of claim 14, wherein the health-related information comprises one or more of initial biometrics, initial health conditions, age or gender of the member.

16. The method of claim 15, wherein the determined reduction in the projected costs is based on updates to the initial biometrics or updates to the initial health conditions of the member.

17. A computer system, the system comprising:
    one more servers configured to:
        receive health-related member information with respect to a member of a health plan;
        apply evidence-based medicine rules to the received health-related member information to determine one or more actions to address the health of the member;
        compare the health-related member information and self-reported member data of the member with the one or more actions to identify completion of one or more actions;
        grant rewards for completion of the actions under a rewards program, the rewards program comprising a sequence of steps including at least one action that is verifiable and at least one action that is non-verifiable, wherein each step in the sequence is associated with a reward, wherein a completed verifiable action is granted a first level of reward and a completed non-verifiable action is granted a second level of reward having a lesser value relative to the first, wherein granting rewards for completion of the actions under a rewards program comprises verifying the completion of the at least one verifiable action by obtaining biometric data from an authenticated biometric device that confirms or denies completion of the at least one verifiable action, wherein the biometric data comprises biometric data selected from the group consisting of blood pressure data, glucose level data, cholesterol data, and weight data, and wherein the authenticated biometric device reports one or more of blood pressure, glucose level, cholesterol, or weight.

18. The system of claim 17, wherein the one or more servers is further configured to:

determine, in response to receiving said health-related information, a projected lifetime healthcare cost for the member; and determining, in response to identifying completed actions, a cost savings in the projected lifetime healthcare cost for the member.

19. A non-transitory computer readable medium storing instructions that when executed by a computer cause the computer to perform operations comprising:

initiating a rewards program comprising a sequence of steps including at least one action that is verifiable and at least one action that is non-verifiable, wherein each step in the sequence is associated with a reward;

for the at least one verifiable action, verifying the completion of the at least one verifiable action to satisfy one or more of the sequence of steps, wherein verifying comprises obtaining biometric data from an authenticated device that confirms or denies completion of the step, wherein the biometric data comprises biometric data selected from the group consisting of blood pressure data, glucose level data, cholesterol data, and weight data, and wherein the authenticated biometric device reports one or more of blood pressure, glucose level, cholesterol, or weight;

for the at least one non-verifiable action, receiving non-verifiable medical information or self-reported member data to satisfy completion of one or more of the sequence of steps; and granting rewards under the rewards program, wherein the at least one completed verifiable action is granted a first level of reward and the at least one completed non-verifiable action is granted a second level of reward having a lesser value relative to the first.

20. The non-transitory computer readable medium of claim 19, further operable to cause the computer to perform operations comprising:

determining, in response to receiving health-related information of a member, a projected lifetime healthcare cost for the member; and determining, in response to identifying completed actions, a cost savings in the projected lifetime healthcare cost for the member.

* * * * *